(12) United States Patent
Panzirer

(10) Patent No.: US 9,199,034 B2
(45) Date of Patent: Dec. 1, 2015

(54) DRUG DELIVERY DEVICES, SYSTEMS, AND METHODS

(75) Inventor: David Panzirer, Katonah, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1313 days.

(21) Appl. No.: 12/896,357

(22) Filed: Oct. 1, 2010

(65) Prior Publication Data

US 2011/0112508 A1 May 12, 2011

Related U.S. Application Data

(60) Provisional application No. 61/259,405, filed on Nov. 9, 2009.

(51) Int. Cl.
*A61M 5/178* (2006.01)
*A61M 5/00* (2006.01)
*A61M 5/158* (2006.01)
*A61M 25/00* (2006.01)
A61M 25/04 (2006.01)

(52) U.S. Cl.
CPC .............. *A61M 5/158* (2013.01); *A61M 25/007* (2013.01); *A61M 25/04* (2013.01); *A61M 2005/1585* (2013.01); *A61M 2005/1587* (2013.01)

(58) Field of Classification Search
CPC ............. A61M 2005/1585; A61M 2005/1587; A61M 25/007; A61M 25/04; A61M 5/158; A61M 25/0043; A61M 5/46; A61M 5/00; A61M 25/0067; A61M 25/0074; A61M 25/0075; A61M 2005/178

USPC ......... 604/174, 175, 180, 264, 116, 117, 272, 604/164.01, 164.04, 167.03, 21, 167.02, 604/506, 151, 246, 164.02, 167.01
See application file for complete search history.

(56) References Cited

U.S. PATENT DOCUMENTS

| | | | | |
|---|---|---|---|---|
| 4,693,257 A * | 9/1987 | Markham | | 600/565 |
| 5,201,723 A | 4/1993 | Quinn | | |
| 5,328,483 A | 7/1994 | Jacoby | | |
| 5,403,291 A | 4/1995 | Abrahamson | | |
| 5,782,811 A | 7/1998 | Samson et al. | | |
| 5,848,991 A * | 12/1998 | Gross et al. | | 604/140 |
| 6,261,272 B1 * | 7/2001 | Gross et al. | | 604/272 |
| 6,517,521 B1 * | 2/2003 | Ly | | 604/239 |
| 6,524,300 B2 | 2/2003 | Meglin | | |
| 6,945,969 B1 | 9/2005 | Morris et al. | | |
| 2002/0156453 A1 * | 10/2002 | Pettis et al. | | 604/506 |
| 2002/0198509 A1 | 12/2002 | Mikszta et al. | | |

(Continued)

*Primary Examiner* — Bhisma Mehta
*Assistant Examiner* — Bradley G Thomas, Jr.
(74) *Attorney, Agent, or Firm* — Dickinson Wright PLLC

(57) ABSTRACT

This disclosure relates to drug delivery devices, systems, and methods. In some aspects, a drug delivery device includes an elongate member defining a fluid passage and an opening in fluid communication with the fluid passage, and a projection extending radially from the elongate member. A portion of the elongate member extending axially from the projection to a distal end of the elongate member has a length sufficient to allow the distal end of the elongate member to reach subdermal tissue of a patient when the elongate member is inserted into the patient and the projection is in contact with an outer surface of skin of the patient, and the opening is positioned at a location along the elongate member such that the opening is disposed within a dermis of the patient when the elongate member is inserted into the patient and the projection is in contact with the outer surface of the skin of the patient.

17 Claims, 4 Drawing Sheets

(56) References Cited

U.S. PATENT DOCUMENTS

| | | |
|---|---|---|
| 2003/0073609 A1 | 4/2003 | Pinkerton |
| 2004/0073160 A1 | 4/2004 | Pinkerton |
| 2004/0092893 A1* | 5/2004 | Haider et al. ............ 604/272 |
| 2004/0162531 A1* | 8/2004 | Wenchell ............ 604/264 |
| 2005/0096630 A1 | 5/2005 | Pettis et al. |
| 2005/0096631 A1 | 5/2005 | Pettis et al. |
| 2005/0096632 A1 | 5/2005 | Pettis et al. |
| 2007/0005017 A1 | 1/2007 | Alchas et al. |
| 2011/0077597 A1* | 3/2011 | Gresham ............ 604/164.03 |

* cited by examiner

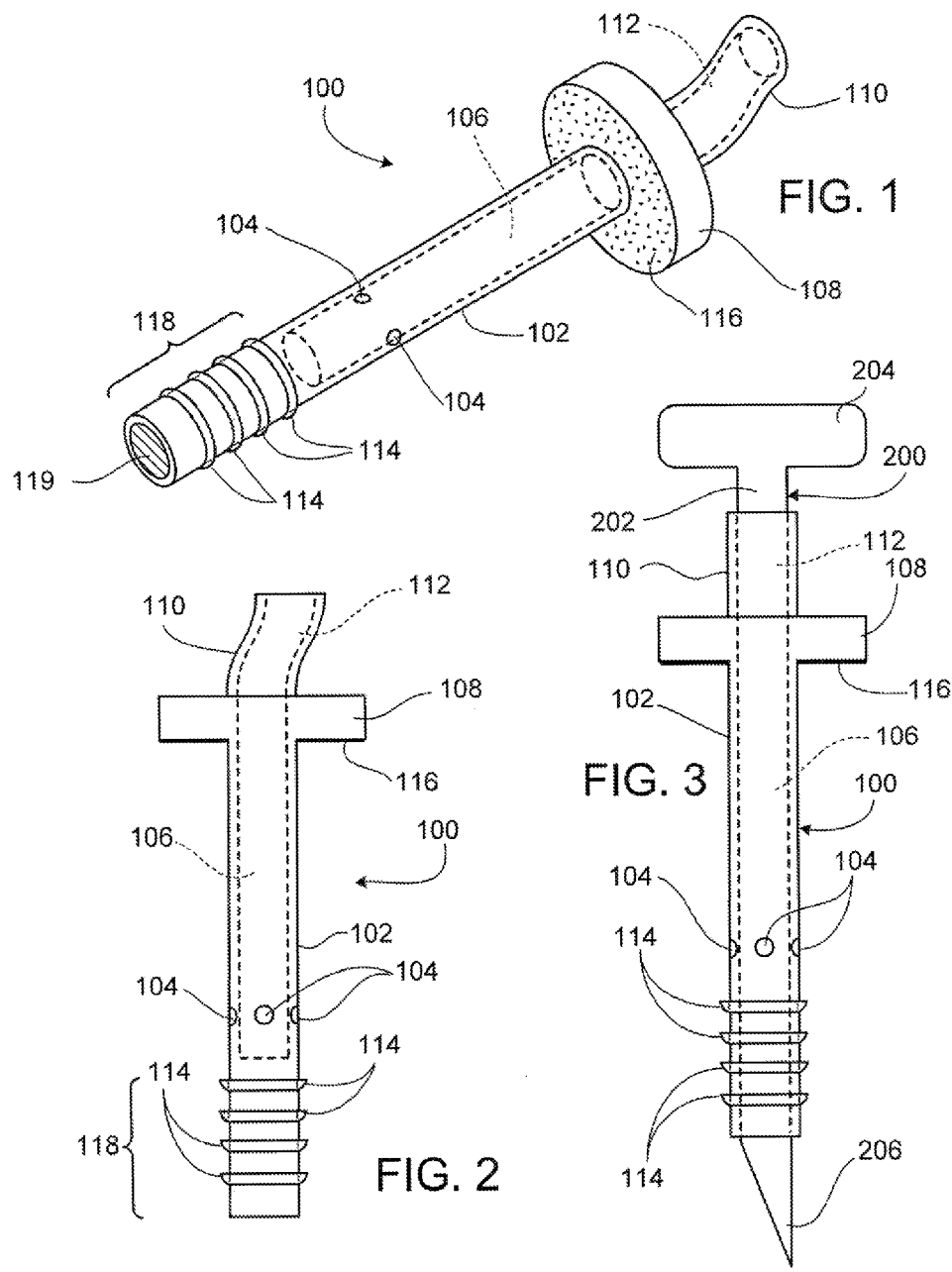

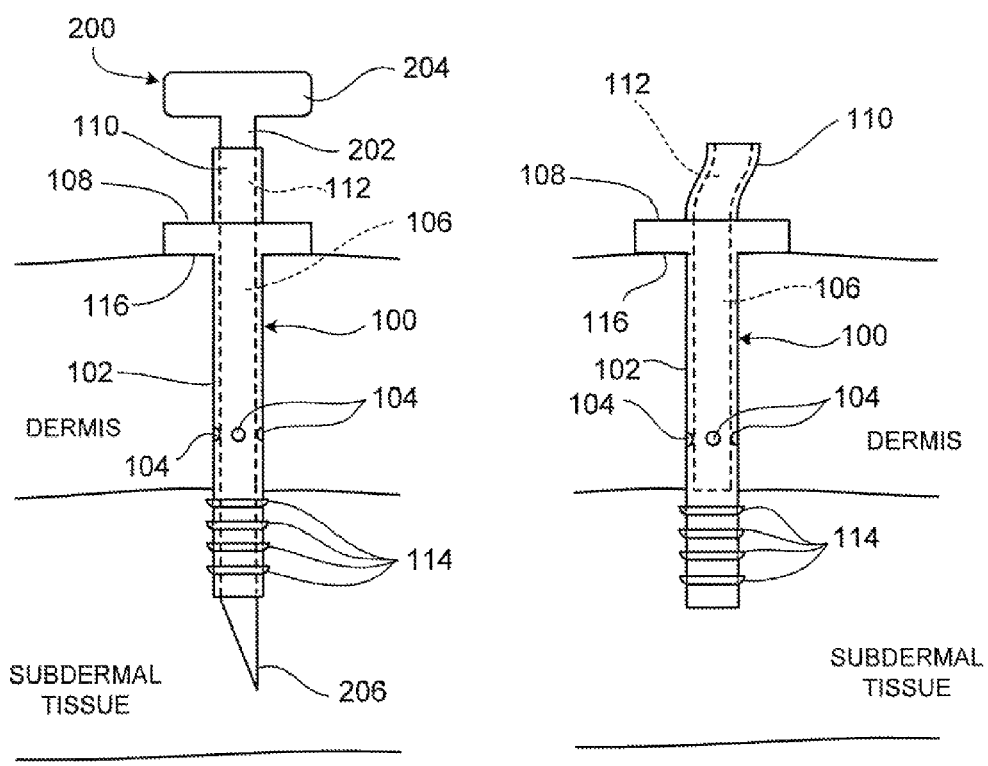

DRUG DELIVERY DEVICES, SYSTEMS, AND METHODS

CROSS-REFERENCE TO RELATED APPLICATIONS

This application claims the benefit under 35 U.S.C. §119 (e) of U.S. application Ser. No. 61/259,405, filed on Nov. 9, 2009, which is incorporated by reference.

TECHNICAL FIELD

This disclosure relates to drug delivery devices, systems, and methods.

BACKGROUND

Drugs can be percutaneously delivered to patients to treat many different medical conditions. In many cases, these drugs are delivered into subdermal tissue. For example, the drugs can be injected via a needle that is inserted into the subdermal tissue of the patient or can be pumped through a catheter that is positioned within the subdermal tissue of the patient. Some drugs can be delivered intradermally (i.e., within the dermis of the patient). Intradermal drug delivery can be carried out, for example, by injecting the drug via a very small needle (i.e., a microneedle) inserted into the dermis of the patient.

SUMMARY

In one aspect of the invention, a drug delivery device includes an elongate member defining a fluid passage and an opening in fluid communication with the fluid passage. A projection extends radially from the elongate member. A portion of the elongate member extending axially from the projection to a distal end of the elongate member has a length sufficient to allow the distal end of the elongate member to reach subdermal tissue of a patient when the elongate member is inserted into the patient and the projection is in contact with an outer surface of skin of the patient, and the opening is positioned at a location along the elongate member such that the opening is disposed within a dermis of the patient when the elongate member is inserted into the patient and the projection is in contact with the outer surface of the skin of the patient.

In another aspect of the invention, a drug delivery device includes an elongate member defining a fluid passage and an opening in fluid communication with the fluid passage. A projection extends radially from the elongate member. A portion of the elongate member extending axially from the projection to a distal end of the elongate member has a length of at least about four millimeters, and the opening is positioned at a location that is axially spaced from the projection by no more than about 2.5 millimeters.

In an additional aspect of the invention, a drug delivery system includes an elongate member defining a fluid passage and an opening in fluid communication with the fluid passage. The system also includes a projection extending radially from the elongate member and a needle configured to extend through the passage and distally beyond a distal end of the elongate member. A portion of the elongate member extending axially from the projection to a distal end of the elongate member has a length sufficient to allow the distal end of the elongate member to reach subdermal tissue of a patient when the needle and the elongate member are inserted into the patient and the projection is in contact with an outer surface of skin of the patient, and the opening is positioned at a location along the elongate member such that the opening is disposed within a dermis of the patient when the elongate member and the needle are inserted into the patient and the projection is in contact with the outer surface of the skin of the patient.

In a further aspect of the invention, a drug delivery system includes an elongate member defining a fluid passage and an opening in fluid communication with the fluid passage. The system also includes a projection extending radially from the elongate member and a needle configured to extend through the passage and distally beyond a distal end of the elongate member. A portion of the elongate member extending axially from the projection to a distal end of the elongate member has a length of at least about four millimeters, and the opening is positioned at a location that is axially spaced from the projection by no more than about 2.5 millimeters.

In yet another aspect of the invention, a drug delivery method includes inserting an elongate member into a patient such that a distal end of the elongate member is positioned in subdermal tissue of the patient, and delivering a drug to a dermis of the patient via the elongate member.

Embodiments can include one or more of the following features.

In some embodiments, the portion of the elongate member extending axially from the projection to a distal end of the elongate member has a length of at least about four millimeters, and the opening is positioned at a location that is axially spaced from the projection by no more than about 2.5 millimeters.

In some embodiments, the portion of the elongate member extending axially from the projection to the distal end of the elongate member has a length of at least about five millimeters (e.g., at least about six millimeters, at least about nine millimeters).

In some embodiments, the portion of the elongate member extending axially from the projection to the distal end of the elongate member has a length of about four millimeters to about nine millimeters (e.g., about four millimeters to about six millimeters, about six millimeters to about nine millimeters).

In some embodiments, the opening is positioned at a location that is axially spaced from the projection by about 0.3 millimeter to about 2.5 millimeters (e.g., about 0.3 millimeter to about two millimeters, about 0.3 millimeter to about one millimeter, about 0.3 millimeter to about 0.5 millimeter).

In some embodiments, a portion of the elongate member between the opening and the distal end of the elongate member includes a self-sealing material (e.g., a polymeric self-sealing material).

In some embodiments, the self-sealing material is capable of forming a substantially liquid-tight seal after a needle having a diameter smaller than a diameter of the passage is inserted through the self-sealing material and then removed.

In some embodiments, a portion of the elongate member between the opening and the distal end of the elongate comprises a valve (e.g., a duckbill valve).

In some embodiments, the valve is capable of forming a substantially liquid-tight seal after a needle having a diameter smaller than a diameter of the passage is inserted through the valve and then removed.

In some embodiments, the drug delivery device further includes at least one feature extending radially from a portion of the elongate member between the opening and the distal end of the elongate member.

In some embodiments, the feature is a barb.

In some embodiments, the barb extends about the entire circumference of the elongate member.

In some embodiments, the passage terminates proximal to the distal end of the elongate member.

In some embodiments, the passage terminates at the opening.

In some embodiments, a distal end region of the elongate member is tapered.

In some embodiments, the elongate member has a sharp distal tip.

In some embodiments, the sharp distal tip is not in fluid communication with the passage.

In some embodiments, the sharp distal tip is capable of piercing the skin of a patient.

In some embodiments, the elongate member defines a plurality of openings in fluid communication with the passage, and the plurality of openings are positioned at locations along the elongate member such that the openings are disposed within the dermis of the patient when the elongate member is inserted into the patient and the projection is in contact with the outer surface of the skin of the patient.

In some embodiments, the plurality of openings are circumferentially spaced around the elongate member.

In some embodiments, the plurality of openings are axially spaced along the elongate member.

In some embodiments, the drug delivery system further includes a drug injection device capable of being placed in fluid communication with the passage of the elongate member.

In some embodiments, the drug injection device includes a pump.

In some embodiments, the drug delivery system further includes a tube connected to the drug injection device and to the elongate member.

In some embodiments, the elongate member defines a passage and an opening in fluid communication with the passage, and delivering the drug to the dermis of the patient comprises delivering the drug through the passage and then out the opening into the dermis.

In some embodiments, delivering the drug through the passage includes running a pump connected to a drug source.

In some embodiments, the pump is connected to the elongate member via a tube.

In some embodiments, the distal end of the elongate member is closed such the drug is prevented from exiting the distal end of the elongate member into the subdermal tissue.

In some embodiments, the elongate member is mounted on a needle when the elongate member is inserted into the patient.

In some embodiments, the drug delivery method further includes removing the needle from the elongate member prior to delivering the drug.

In some embodiments, the elongate member has a sharp distal tip that punctures the skin as the elongate member is inserted into the patient.

In some embodiments, the drug is insulin.

Embodiments can include one or more of the following advantages.

In some embodiments, the elongate member of the drug delivery device is sized such that the distal end of the elongate member is positioned in the subdermal tissue of a patient when the radial projection is in contact with the outer surface of the patient's skin, and the opening of the elongate member is located along a region of the elongate member that sits within the dermis of the patient when the radial projection is in contact with the outer surface of the patient's skin. This configuration permits drugs to be delivered to the dermis of the patient. This configuration also provides increased resistance to the catheter slipping out of the patient (as compared to arrangements in which the distal end of a drug delivery member rests within the dermis of the patient). As a result, the patient can enjoy various benefits of intradermal drug delivery while being confident that the elongate member will not become inadvertently dislodged from the patient during normal conditions of use.

In certain embodiments, the drug delivery device is used to deliver drugs intradermally to a patient (i.e., into the dermis of a patient). Intradermal drug delivery can allow the drugs to be absorbed much more quickly by the patient than drugs delivered into subdermal tissue. Thus, for certain drugs, the effects of the drugs can be experienced and/or felt by the patient faster when the drugs are intradermally delivered than when the drugs are delivered into the subdermal tissue of the patient.

In some embodiments, the distal end of the elongate member is closed such that drug can only be delivered to the patient via the openings that are arranged to be positioned in the dermis of the patient during use. Delivering all of the drug into the dermis can be advantageous. For example, delivery of all of the drug intradermally can help to ensure that all of the drug is absorbed by the patient at a similar rate (e.g., at substantially the same rate).

Other aspects, features, and advantages will be apparent from the description and drawings, and from the claims.

DESCRIPTION OF DRAWINGS

FIG. 1 is a perspective view of a drug delivery device that can be used to deliver a drug into the dermis of a patient.

FIG. 2 is a side view of the drug delivery device of FIG. 1.

FIG. 3 is a side view of the drug delivery device of FIG. 1 mounted on a needle that can be used to temporarily implant an elongate member of the drug delivery device within a patient.

FIGS. 4-6 schematically illustrate a method of using the drug delivery device of FIG. 1 to deliver a drug into the dermis of a patient.

DETAILED DESCRIPTION

Figure 6:
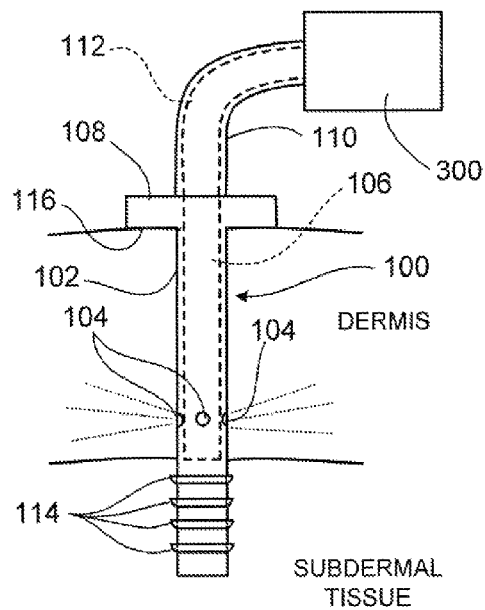

Referring to FIGS. 1 and 2, a drug delivery device 100 includes an elongate member 102 in which multiple circumferentially spaced openings 104 are formed. The openings 104 are in fluid communication with a central passage 106 that extends axially within the elongate member 102. An annular projection 108 extends radially from a proximal end region of the elongate member 102. A tube 110 is fluidly connected to the proximal end region of the elongate member 102. In particular, a passage 112 that extends axially within the tube 110 is in fluid communication with the central passage 106 of the elongate member 102. As discussed in greater detail below, the drug delivery device 100 can be used to deliver a drug into the dermis of a patient. In particular, the drug delivery device 100 can be positioned such that a distal end region of the elongate member 102 is positioned within subdermal tissue of the patient and the openings 104 are positioned within the dermis of the patient. The tube 112 can then be connected to a drug injection device (e.g., a drug pump) that can be operated to deliver a drug to the dermis of the patient via the passages 112, 106 and the openings 104.

As shown in FIGS. 1 and 2, the central passage 106 of the elongate member 102 extends from the proximal end of the elongate member 102 to the region of the elongate member 102 in which the openings 104 are formed. A distal portion 118 of the elongate member 102 (i.e., the portion of the elongate member 102 distal to the openings 104) includes no such passage. The distal portion 118 of the tubular body of the elongate member 102 is filled with a self-sealing material (e.g., a plug formed of a self-sealing material) 119 such that after a needle of a desired size is passed through the distal portion 118 of the elongate member 102 and then removed, the self-sealing material in the distal portion 118 of the elongate member 102 essentially returns to its original shape to inhibit (e.g., substantially prevent) liquid passing through the passage 106 from exiting the distal end of the elongate member 102. Examples of such self-sealing materials include certain polymers.

Still referring to FIGS. 1 and 2, the distal end region of the elongate member 102 includes multiple axially spaced annular barbs 114. The barbs 114 extend upward (i.e., toward the proximal end of the elongate member 102) at an acute angle. The barbs 114 can, for example, extend upward at an angle of about 45 degrees or less (e.g., about 30 degrees or less, about 15 degrees or less) relative to the longitudinal axis of the elongate member 102. As a result of this design, the barbs 114 permit the elongate member 102 to easily pass through the skin of the patient when the drug delivery device 100 is being inserted into the patient but provides greater resistance to the elongate member 102 being pulled out of the patient's skin in the opposite direction. Thus, the barbs 114 help to prevent the elongate member 102 from inadvertently being pulled out of the patient during use.

The annular projection 108 extends a sufficient distance radially from the elongate member 102 to abut the outer surface of the patient's skin and to prevent portions of the drug delivery device 100 proximal of the annular projection 108 from entering the patient when the elongate member 102 is inserted into the patient. The annular projection 108 is positioned at a location along the length of the elongate member 102 to permit a desired length of the elongate member 102 to penetrate the patient's skin. The length of the elongate member 102 and the position of the annular projection 108 along the elongate member 102 are selected so that the distal end of the elongate member 102 sits within the subdermal tissue of the patient when annular projection 108 is in contact with the outer surface of the patient's skin. In some embodiments, the portion of the elongate member 102 extending from the distal surface of the annular projection 108 to the distal end of the elongate member 102 has a length of at least about four millimeters (e.g., at least about five millimeters, at least about six millimeters, at least about nine millimeters). In certain embodiments, the portion of the elongate member 102 extending from the distal surface of the annular projection 108 to the distal end of the elongate member 102 has a length of about four millimeters to about nine millimeters (e.g., about four millimeters to about six millimeters, about six millimeters to about nine millimeters).

The openings 104 of the elongate member 102 are positioned at a location along the elongate member 102 such that the openings 104 sit within the dermis of the patient when the annular projection 108 is in contact with the outer surface of the patient's skin. In some embodiments, the openings 104 are positioned no more than about 2.5 millimeters (e.g., no more than about two millimeters, no more than about one millimeter, no more than about 0.5 millimeter, no more than about 0.4 millimeter, no more than about 0.3 millimeter) from the annular projection 108 of the elongate member 102. In certain embodiments, the openings 104 are positioned about 0.3 millimeter to about 2.5 millimeters (e.g., about 0.3 millimeter to about two millimeters, about 0.3 millimeter to about one millimeter, about 0.3 millimeter to about 0.5 millimeter) from the annular projection (e.g., from the distal surface of the annular projection).

As shown in FIGS. 1 and 2, the annular projection 108 includes adhesive 116 on its distal surface (i.e., the surface facing the distal end region of the elongate member 102). The adhesive 116 adheres the annular projection 108 to the outer surface of the patient's skin when the drug delivery device 100 is implanted in a desired manner within the patient. The adhesive can help to limit movement of the drug delivery device 100 relative to the patient and can thus help to prevent the drug delivery device 100 from becoming dislodged from the patient during use.

In certain embodiments, the annular projection 108 is integrally formed with the elongate member 102. In other embodiments, the annular projection 108 is a separate annular member that is attached to the elongate member 102. In embodiments in which the annular projection 108 is a separate component from the elongate member 102, any of various attachment techniques, including thermal bonding techniques, adhesive bonding techniques, and mechanical fastening techniques can be used to secure the annular member to the elongate member 102.

The elongate member 102, the annular projection 108, and the tube 110 of the drug delivery device 100 can be formed of one or more medical grade polymers. In certain embodiments, each of these components of the drug delivery device 100 is formed of the same material(s). Alternatively, these components can be formed of different materials. In some embodiments, for example, the tube 110 is formed of a more flexible material than the elongate member 102 and annular projection 108. In certain embodiments, the elongate member 102 and/or the annular projection 108 of the drug delivery device 100 is/are formed of one or more metals, such as stainless steel.

Any of various manufacturing techniques, including injection molding, etching, and machining, can be used to form the components of the drug delivery device 100. In certain embodiments, the components of the drug delivery device are integrally molded with one another. The elongate member 102, annular projection 108, and tube 110 can, for example, be injection molded in two halves and then the two halves can be attached (e.g., thermally bonded or adhesively bonded) to one another. The self-sealing material 119 can be in the form of a plug that is inserted into the distal end region of the elongate member 102 during the manufacturing process. Alternatively, the self-sealing material 119 can be injected into the distal end region 118 of the elongate member 102.

Referring to FIG. 3, in order to implant the elongate member 102 of the drug delivery device 100 within a patient, a needle assembly 200 including a needle 202 and a handle 204 is passed through the tube 110, the annular projection 108, and the elongate member 102 of the drug delivery device 100 until a sharp tip 206 of the needle 202 extends distally beyond the distal end of the elongate member 102. To achieve this configuration, the needle 202 is passed through the passages 112 and 106 of the tube 110 and the elongate member 102, respectively, until the sharp tip 206 of the needle 202 punctures the self-sealing material 119 in the distal portion 118 of the elongate member 102. The user then continues to apply a force to the needle 202 to pass the needle tip 206 through the resilient self-sealing material 119 in the distal portion 118 and beyond the distal end of the elongate member 102.

FIGS. 4-6 schematically illustrate a method of using the drug delivery device 100 to deliver a drug to the dermis of a patient. Referring to FIG. 4, with the needle assembly 200 positioned in the drug delivery device 100, the needle 202 of the needle assembly 200 and the elongate member 102 of the drug delivery device 100 are inserted into the patient. In particular, the needle 202 and the elongate member 102 are forced into the patient until the annular projection 108 of the drug delivery device 100 contacts the outer surface of the patient's skin. Because the sharp tip 206 of the needle 202 extends distally beyond the distal end of the elongate member 102, the needle 202 facilitates the passage of the elongate member 102 through the skin of the patient. In particular, the needle 202 creates a puncture hole through which the elongate member 102 passes as the user applies a downward force to the handle 204 of the needle assembly 200. As shown in FIG. 4, when the annular projection 108 abuts the outer surface of the patient's skin, the sharp tip 206 of the needle 202 and the distal end of the elongate member 102 are disposed in the subdermal tissue of the patient, and the openings 104 of the elongate member 102 are disposed in the dermis of the patient.

Once the distal end of the elongate member 102 has been positioned in the subdermal tissue and the openings 104 have been positioned in the dermis, the needle assembly 200 is removed from the drug delivery device 100, leaving the elongate member 102 of the drug delivery device 100 implanted within the patient, as shown in FIG. 5. To remove the needle assembly 200 from the drug delivery device 100, the user grasps the handle 204 of the needle assembly 200 and pulls the needle assembly 200 in a direction away from the patient. The adhesion of the adhesive on the distal surface of the annular projection 108 to the outer surface of the patient's skin helps to prevent the drug delivery device 100 from being pulled out of the patient along with the needle assembly 200. The annular barbs 114 along the distal portion 118 of the elongate member 102 also help to prevent the drug delivery device 100 from bring pulled out of the patient along with the needle assembly 200. In addition, the user may apply a downward force to the drug delivery device 100 as the needle assembly 200 is removed to prevent movement of the drug delivery device 100 relative to the patient. As the needle 202 is removed from the distal portion 118 of the elongate member 102, the resilient self-sealing material 119 of the distal portion 118 returns to its original configuration and thus closes the passage that was created therethrough by the needle.

Referring to FIG. 6, after removing the needle assembly 200 from the drug delivery device 100, the tube 110 of the drug delivery device 100 is connected to a drug pump 300. The drug pump 300 is then operated to force a drug through the passages 112 and 106 of the tube 110 and the elongate member 102, respectively, and out the openings 104 into the dermis. Because the resilient self-sealing material 119 of the distal portion 118 of the elongate member 102 returned to its original shape after the needle 202 was removed from the drug delivery device 100, the drug delivered through the passages 112, 106 and the openings 104 is substantially prevented from exiting the distal end of the elongate member 102. As a result, the drug is delivered only within the dermis of the patient. By delivering the drug only into the dermis of the patient, the rate at which the drug will be absorbed by the patient can be more easily predicted than if the drug had been delivered to both the dermis and the subdermal tissue of the patient. In addition, with certain drugs (e.g., insulin), delivering the drug only into the dermis of the patient can increase the overall rate at which the drug is absorbed by the patient, as compared to delivery methods in which the drug is delivered into the subdermal tissue or some other tissue of the patient. Thus, delivering the drug into the dermis of the patient can reduce (e.g., minimize) the length of time required for the drug to reach is maximum level of effectiveness.

In some embodiments, the drug pump 300 is a portable pump that can be carried by the patient during operation. The drug pump 300 can, for example, be carried in a pocket of the patient's clothing or can be taped or otherwise secured to the patient's body. While this arrangement provides the patient with the convenience of mobility, forces applied to the drug delivery device 100 (e.g., to the tube 110 of the drug delivery device 100) during physical activity of the patient increase the risk of the elongate member 102 being inadvertently pulled out of the patient. Because the length of the portion of the elongate member 102 distal to the annular projection 108 is sufficient to permit the distal portion 118 (e.g., a portion of the distal portion 118) of the elongate member 102 to be positioned within the subdermal tissue of the patient, the elongate member 102 is less likely to become inadvertently dislodged from the patient during use, as compared to shorter catheters or needles that terminate within the dermis of the patient. For example, the increased fiction (due to the increased length of the elongate member 102) relative to shorter catheters or needles can improve the ability of the elongate member to remain lodged within the patient.

In addition to those characteristics of the elongate member 102 discussed above that help to ensure that the elongate member 102 does not become inadvertently dislodged from the patient during use, the distal portion 118 of the elongate member 102 is also provided with the annular barbs 114. Because the annular barbs 114 extend at an upward angle relative to the elongate member 102 (i.e., at an acute angle relative to the longitudinal axis of the elongate member 102), the annular barbs 114 catch on tissue and thus provide resistance when the elongate member 102 is pulled in a direction away from the patient. Thus, the annular barbs 114 further help to ensure that the elongate member 102 does not become inadvertently dislodged from the patient during use. This helps to ensure that the all of the desired drug is able to be delivered through the openings 104 and into the dermis of the patient during treatment.

Any of various different types of drugs can be delivered to the dermis of the patient using the delivery method described above. Examples of such drugs include peptides, proteins, hormones, analgesics, anti-migraine agents, anti-coagulant agents, anti-emetic agents, cardiovascular agents, anti-hypertensive agents, narcotic antagonists, chelating agents, anti-anginal agents, chemotherapy agents, sedatives, anti-neoplastics, prostaglandins, antidiuretic agents, and vaccines. Examples of peptides, proteins or hormones include insulin, calcitonin, calcitonin gene regulating protein, atrial natriuretic protein, colony stimulating factor, betaseron, erythropoietin (EPO), interferons (e.g., α, β, or γ interferon), somatropin, somatotropin, somatostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues thereof. Examples of analgesics include fentanyl, sufentanil, butorphanol, buprenorphine, levorphanol, morphine, hydromorphone, hydrocodone, oxymorphone, methadone, lidocaine, bupivacaine, diclofenac, naproxen, paverin, and analogues thereof. Examples of anti-migraine agents include sumatriptan, ergot alkaloids, and analogues thereof. Examples of anti-coagulant agents include heparin, hirudin, and analogues thereof. Examples of anti-emetic agents include scopolamine, ondansetron, domperidone, metoclopramide, and analogues thereof. Examples of cardiovascular agents, anti-hypertensive agents and vasodilators include diltiazem, clonidine, nifedipine, verapamil, isosorbide-5-mononitrate, organic nitrates, agents used in treatment of heart disorders, and analogues thereof. Examples of sedatives include benzodiazepines, phenothiozines, and analogues thereof. Examples of narcotic antagonists include naltrexone, naloxone, and analogues thereof. Examples of chelating agents include deferoxamine, and analogues thereof. Examples of anti-diuretic agents include desmopressin, vasopressin, and analogues thereof. Examples of anti-anginal agents include nitroglycerine, and analogues thereof. Examples of anti-neoplastics include 5-fluorouracil, bleomycin, and analogues thereof. Examples of chemotherapy agents include vincristine and analogues thereof.

The drug delivery device 100 is constructed as a disposable, single-use device. Thus, after completing the drug delivery process, the tube 110 is disconnected from the pump 300, the elongate member 102 is pulled out of the patient, and the drug delivery device 100 is discarded.

While certain embodiments have been described, other embodiments are possible.

While the distal portion 118 of the elongate member 102 has been described as being filled with a self-sealing material, any of various other techniques that allow a needle to be passed through the distal portion 118 of the elongate member 102 and then substantially prevent liquids being passed through the central passage 106 of the elongate member 102 from exiting the distal end of the elongate member 102 after the needle is removed can be used. In some embodiments, for example, the distal portion 118 of the elongate member 102 includes a passage that extends therethrough and a duckbill valve positioned along the passage. The duckbill valve is constructed to allow a needle to pass through the duckbill valve and then to seal shut after the needle has been removed from the duckbill valve. Any of various other types of valves that are capable of allowing a needle to pass therethrough and then closing in a manner to substantially prevent a drug passing through the central passage 106 of the elongate member 102 from exiting the distal end of the elongate member 102 after the needle is removed may alternatively or additionally be used.

While the elongate member 102 has been described as including annular barbs to help prevent the elongate member 102 from being inadvertently pulled out of the patient, other types of barbs can alternatively or additionally be used. The elongate member 102 can, for example, include discrete barbs that extend from the side wall of the elongate member 102. Such discrete barbs are limited to only a portion of the circumference of the elongate member 102 rather than extending about the entire circumference of the elongate member 102.

While the elongate member 102 of the drug delivery device 100 includes barbs 114, in certain embodiments, the elongate member 102 includes no barbs. In such embodiments, for example, the length of the elongate member can be selected to provide sufficient resistance to prevent the elongate member from being inadvertently pulled out of the patient during use. The length of the elongate member can, for example, be selected so that a desired length of the elongate member can be inserted into the subdermal tissue of a patient. In some embodiments, at least one millimeter (e.g., at least two millimeters, at least three millimeters, at least four millimeters, at least five millimeters, at least six millimeters) of the elongate member can be inserted into the subdermal tissue of the patient.

While the drug delivery device 100 has been described as including the annular projection 108, the drug delivery device 100 can alternatively or additionally be equipped with other types of structures fir limiting the depth to which the elongate member 102 is inserted into the patient. For example, the elongate member 102 can be equipped with one or more discrete radial projections (i.e., radial projections that extend about only a portion of the circumference of the elongate member 102). Alternatively, the drug delivery device 100 can include no such depth limiting structure. Instead, for example, the elongate member 102 can include markers (e.g., marker rings) along its outer surface that indicate to the user how far into the patient the elongate member 102 has been inserted. Such markers can, for example, be arranged to indicate the length between the marker and the distal end of the elongate member 102 such that when a particular marker is aligned with the outer surface of the patient's skin, the user knows how far into the patient the elongate member has been inserted. Such an arrangement, like the depth limiting structures discussed above, can help to ensure that the distal end of the elongate member 102 is inserted into the subdermal tissue of the patient during use.

While the elongate member 102 has been illustrated as having a substantially constant diameter along its length, in certain embodiments, the diameter of the elongate member 102 changes along its length. The distal portion 118 of the elongate member 102 can, for example, taper inwardly toward the distal end of the elongate member 102 to increase the ease with which the elongate member 102 can be inserted into a patient.

Figure 7:
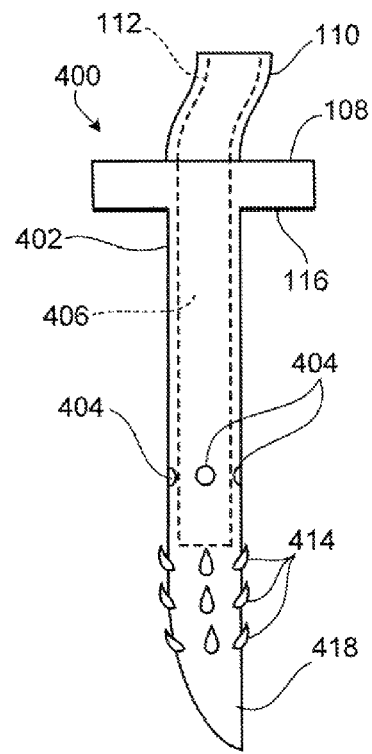
FIG. 7 is a side view of another drug delivery device that includes an elongate member with discrete barbs along its length to help retain the elongate member within a patient during use.

While the drug delivery device 100 is configured to cooperate with the needle assembly 200 in order to implant the elongate member 102 of the drug delivery device 100 within the patient, other configurations are possible. In some embodiments, as shown in FIG. 7, for example, a drug delivery device 400 includes an elongate member 402 with a sharpened distal tip 418. In certain embodiments, the elongate member 402, including the sharpened distal tip 418, is formed of a rigid polymer or a metal, such as stainless steel. The rigidity of the elongate member 402 and the sharpness of the tip 418 facilitates passage through the skin and tissue of a patient. Similar to the drug delivery device 100, the drug delivery device 400 includes the annular projection 108 near a proximal end of the elongate member 402 and the tube 110 arranged so that the fluid passage 112 of the tube 110 is in fluid communication with a fluid passage 406 formed in the elongate member 402. The elongate member 402 also includes openings 404 that are circumferentially spaced around the elongate member 402 such that one or more drugs can be passed through the passages 112 and 406 and through the openings 404 into the patient (e.g., into the dermis of the patient) during use. As shown in FIG. 7, the passage 406 ends in the proximity of the openings 404 and does not extend to the distal tip 418 of the elongate member 402. Because the sharpened tip 418 includes no openings and no passage, the drug delivered through the drug delivery device 400 is not allowed to pass through the distal tip 418 and into the patient. Rather, the drug delivery is localized to the tissue adjacent the openings 404. The elongate member 402 also includes multiple circumferentially spaced and axially spaced barbs 414 that help to prevent slippage of the elongate member 402 when it is implanted within the patient.

To use the drug delivery device 400 to deliver a drug to a patient, the user grasps the annular projection 108 and forces the sharpened distal tip 418 of the elongate member 402 into the patient's skin. Because the distal tip 418 of the elongate member 402 is sharpened, there is no need to use a separate tool, such as a needle, to puncture the patient's skin. After inserting the elongate member 402 to a depth such that the distal end of the elongate member 102 resides in the subdermal tissue of the patient and the openings 404 reside within the dermis of the patient, the drug is delivered to the dermis of the patient via the passages 112, 406 and the openings 404. After the delivery process is complete, the drug delivery device 400 is removed from the patient and discarded.

While each of the drug delivery devices described above includes an elongate member that defines circumferentially spaced openings, the elongate member of any of the devices described herein can alternatively or additionally define axially spaced openings (i.e., openings that are spaced along the length of the elongate members). Two or more (e.g., three or more, four or more, five or more) openings can be provided along the length of the elongate member. In some embodiments, the axially spaced openings are arranged so that each of the openings is positioned within the dermis of the patient when the elongate member is inserted to a desired a depth within the patient.

Similarly, while each of the drug delivery devices described above includes an elongate member having multiple openings, the elongate member can alternatively include only a single opening. The opening can, for example, be arranged to be positioned within the dermis of the patient when the elongate member is inserted to a desired a depth within the patient.

While the annular projection 108 has been described as having adhesive on its distal surface, it should be understood that an annular projection with no such adhesive could alternatively be used.

Figure 8:
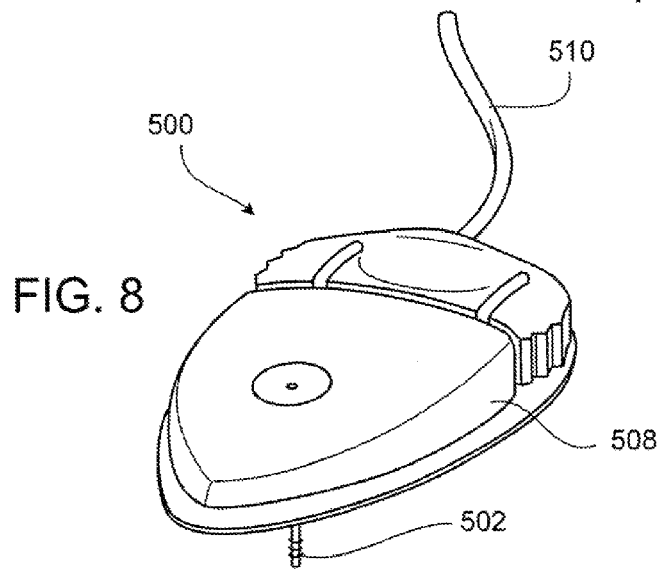
FIG. 8 is a perspective view of another drug delivery device that can be used for delivering a drug into the dermis of a patient.
Figure 9:
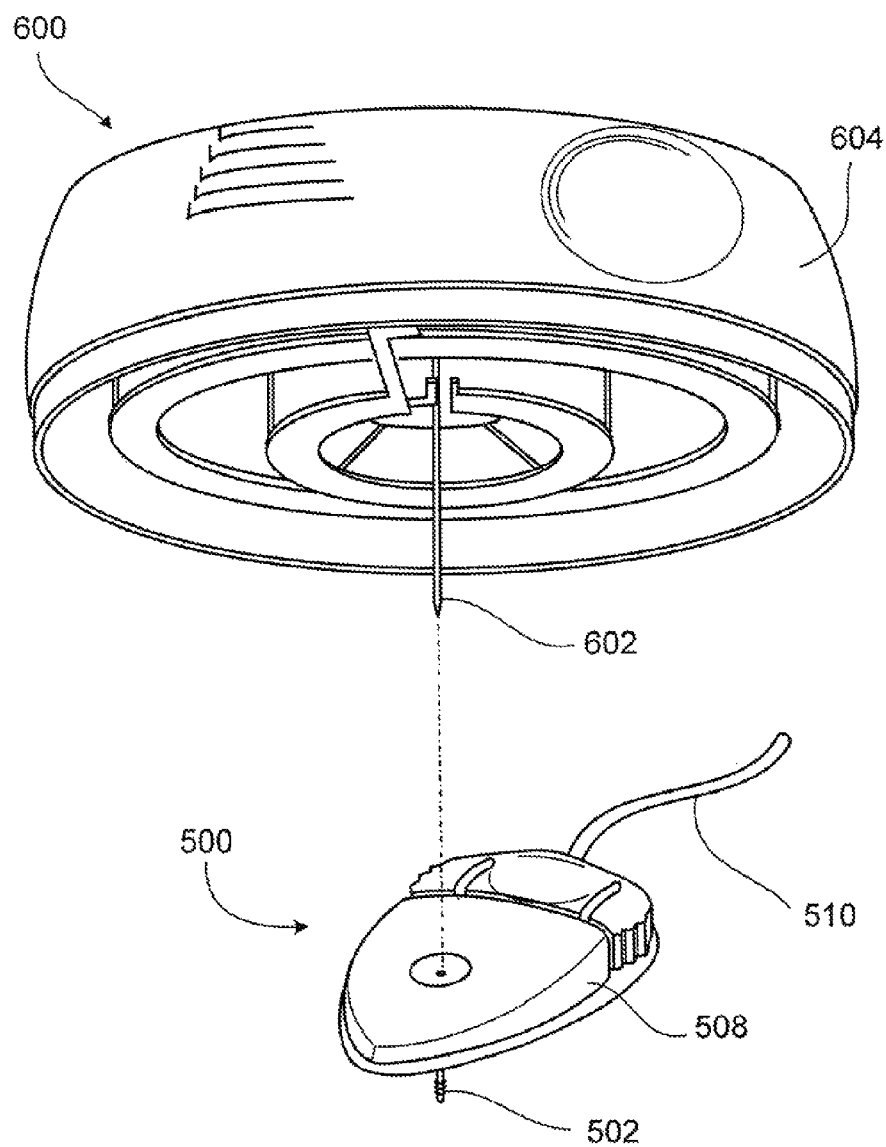
FIG. 9 is an exploded perspective view of a drug delivery system including the drug delivery device of FIG. 8 and a needle assembly on which the drug delivery device can be mounted to temporarily implant an elongate member of the drug delivery device within a patient.

While certain drug delivery systems herein have been described as including the needle assembly 200, which is used to insert the drug delivery device into the patient, other types of needle assemblies can be used. Similarly, the shape and construction of the drug delivery device can vary depending on the type of needle assembly to be used to insert the drug delivery device into the patient. FIG. 8 illustrates a drug delivery device 500, and FIG. 9 illustrates an exploded view of the drug delivery device 500 in combination with a needle assembly 600. The drug delivery device 500 includes an elongate member 502 extending from a base 508 and a tube 510 extending from the base 508. The elongate member 502 and the tube 510 are fluidly connected to one another within the base 508. Referring to FIG. 9, unlike the needle assembly 200 discussed above, the needle assembly 600 includes a puck-shaped housing 604 to which a needle 602 is connected. To perform a drug delivery process using the drug delivery device 500, the drug delivery device 500 is loaded onto the needle assembly 600 such that the needle 602 extends through the elongate member 502 of the drug delivery device 500. Typically, the drug delivery device 500 is loaded onto the needle assembly 600 in this manner prior to being supplied to the end user (i.e., the medical professional or patient). The user then presses the needle assembly 600 against the outer surface of the patient's skin such that the elongate member 502 and the needle 602 penetrate the skin of the patient. Adhesive on the distal surface of the base 508 can help to secure the drug delivery device 500 to the patient at this point. The needle assembly 600 is then removed from the patient and the drug delivery device 500, leaving the elongate member 502 of the drug delivery device 500 implanted within the patient. The tube 510 is then connected to a drug pump, which is operated to deliver a drug to the patient. After the drug delivery process is complete, the drug delivery device 500 is removed from the patient and discarded.

It should be understood that the delivery processes referred to herein can include more than one delivery of the drug. In certain cases, the elongate member of the drug delivery device remains implanted in the patient for an extended period of time (e.g., 12 hours or more, 24 hours or more, one week or more) and drug is delivered to the patient via the drug delivery device multiple times during that extended period of time.

While the drug delivery systems above have been described as being used with a drug pump to force the drug through the drug delivery device, other types of drug injection devices, such as syringes, can alternatively or additionally be used to force the drug through the drug delivery device.

While the drug delivery devices described above are disposable, single-use devices, the drug delivery devices can alternatively be constructed as a reusable device that can be sterilized after the completion of each drug delivery process.

While the methods above involve delivering a drug to only the dermis of a patient, in some embodiments, the drug can be delivered to both the dermis and subdermal tissue. In such embodiments, the openings in the side will of the elongate member can be arranged such that one or more of the openings is positioned in the dermis of the patient and one or more of the openings is positioned in the subdermal tissue of the patient when the elongate member is inserted to a desired a depth within the patient. In certain embodiments, the size of the openings decreases toward the distal end of the elongate member to ensure that a sufficient amount of drug is delivered to the dermis via the larger openings positioned closer to the proximal end of the elongate member. In some embodiments, the passage extending within the elongate member extends from the proximal end to the distal end of the elongate member such that the drug is allowed to flow out the distal end of the elongate member and into the subdermal tissue of the patient. In such embodiments, the diameter of the passage can decrease in the distal direction to ensure that sufficient fluid pressure is achieved within the passage to force some of the drug out of the opening or openings positioned within the dermis of the patient.

Other embodiments are within the scope of the following claims.

What is claimed is:

1. A drug delivery device, comprising:
an elongate member defining a fluid passage and an opening in fluid communication with the fluid passage;
an introducer needle disposable within the elongate member for insertion of the elongate member into a patient's skin; and
a projection extending radially from the elongate member, wherein a portion of the elongate member extending axially from the projection to a distal end of the elongate member has a length sufficient to allow the distal end of the elongate member to reach subdermal tissue of a patient when the elongate member is inserted into the patient and the projection is in contact with an outer surface of skin of the patient, and the opening is positioned at a location along the elongate member such that the opening is disposed within a dermis of the patient when the elongate member is inserted into the patient and the projection is in contact with the outer surface of the skin of the patient; and wherein a portion of the elongate member between the opening and the distal end of the elongate member comprises a self-sealing material to seal the distal end of the elongate member subsequent to removal of the introducer needle.

2. The drug delivery device of claim 1, wherein the portion of the elongate member extending axially from the projection to a distal end of the elongate member has a length of at least about four millimeters, and the opening is positioned at a location that is axially spaced from the projection by no more than about 2.5 millimeters.

3. The drug delivery device of claim 2, wherein the portion of the elongate member extending axially from the projection to the distal end of the elongate member has a length of at least about five millimeters.

4. The drug delivery device of claim 1, wherein the portion of the elongate member extending axially from the projection to the distal end of the elongate member has a length of about four millimeters to about nine millimeters.

5. The drug delivery device of claim 1, wherein the opening is positioned at a location that is axially spaced from the projection by about 0.3 millimeter to about 2.5 millimeters.

6. The drug delivery device of claim 1, wherein the self-sealing material comprises a polymeric material.

7. The drug delivery device of claim 1, further comprising at least one feature extending radially from the portion of the elongate member between the opening and the distal end of the elongate member.

8. The drug delivery device of claim 7, wherein the feature comprises a barb.

9. The drug delivery device of claim 1, wherein the passage terminates proximal to the distal end of the elongate member.

10. The drug delivery device of claim 9, wherein the passage terminates at the opening.

11. The drug delivery device of claim 1, wherein the elongate member has a sharp distal tip.

12. The drug delivery device of claim 11, wherein the sharp distal tip is not in fluid communication with the passage.

13. The drug delivery device of claim 1, wherein the elongate member defines a plurality of openings in fluid communication with the passage, and the plurality of openings are positioned at locations along the elongate member such that the openings are disposed within the dermis of the patient when the elongate member is inserted into the patient and the projection is in contact with the outer surface of the skin of the patient.

14. The drug delivery device of claim 13, wherein the plurality of openings are circumferentially spaced around the elongate member.

15. The drug delivery device of claim 13, wherein the plurality of openings are axially spaced along the elongate member.

16. A drug delivery device, comprising:
an elongate member defining a fluid passage and an opening in fluid communication with the fluid passage;
an introducer needle disposable within the elongate member for insertion of the elongate member into a patient's skin; and
a projection extending radially from the elongate member, wherein a portion of the elongate member extending axially from the projection to a distal end of the elongate member has a length sufficient to allow the distal end of the elongate member to reach subdermal tissue of a patient when the elongate member is inserted into the patient and the projection is in contact with an outer surface of skin of the patient, and the opening is positioned at a location along the elongate member such that the opening is disposed within a dermis of the patient when the elongate member is inserted into the patient and the projection is in contact with the outer surface of the skin of the patient; and
wherein a portion of the elongate member between the opening and the distal end of the elongate member comprises a valve to seal the distal end of the elongate member subsequent to removal of the introducer needle.

17. A drug delivery device, comprising:
an elongate member having a fluid passage;
an introducer needle insertable within the elongate member to assist in insertion of the elongate member into a patient's skin; and
a projection that extends radially from the elongate member and that contacts the skin and limits the depth of the insertion of the distal end of the elongate member to the level of subdermal tissue;
wherein the elongate member has an opening along the fluid passage that is located at a dermis level of the tissue while the projection is contacting the skin; and
wherein the device further comprises a valve disposed in the elongate member between the distal end and the opening of the elongate member.

* * * * *